US012552657B2

(12) United States Patent
Apodaca, Jr. et al.

(10) Patent No.: US 12,552,657 B2
(45) Date of Patent: Feb. 17, 2026

(54) STERILE FILLING METHOD FOR ADDITIVE PRODUCT CONTAINERS

(71) Applicant: Vessl, Inc., Tempe, AZ (US)

(72) Inventors: Walter D. Apodaca, Jr., Chandler, AZ (US); Aaron Dale Harris, Gilbert, AZ (US)

(73) Assignee: VESSL, INC., Tempe, AZ (US)

(*) Notice: Subject to any disclaimer, the term of this patent is extended or adjusted under 35 U.S.C. 154(b) by 0 days.

(21) Appl. No.: 18/362,438

(22) Filed: Jul. 31, 2023

(65) Prior Publication Data

US 2025/0042709 A1 Feb. 6, 2025

(51) Int. Cl.

| | |
|---|---|
| ***A61L 2/06*** | (2006.01) |
| ***A23B 70/30*** | (2025.01) |
| ***B65B 55/06*** | (2006.01) |
| ***B65B 55/14*** | (2006.01) |
| ***B67C 7/00*** | (2006.01) |

(52) U.S. Cl.

CPC ............ *B67C 7/0073* (2013.01); *A23B 70/30* (2025.01); *A61L 2/06* (2013.01); *B65B 55/06* (2013.01); *B65B 55/14* (2013.01); *A61L 2202/23* (2013.01); *B65B 2220/14* (2013.01)

(58) Field of Classification Search

CPC ....... A23B 70/30; A61L 2/06; A61L 2202/23; B65B 55/06; B65B 55/14; B65B 3/06; B65B 31/047; B65B 2220/14; B67C 7/0073

See application file for complete search history.

(56) References Cited

U.S. PATENT DOCUMENTS

| | | | | |
|---|---|---|---|---|
| 2,855,006 A * | 10/1958 | Geisler | .................... | B65B 31/08 141/11 |
| 3,643,586 A * | 2/1972 | Robinson | ................ | B65B 55/06 53/86 |
| 3,891,779 A * | 6/1975 | Robinson | ................ | B65B 55/06 426/399 |

(Continued)

FOREIGN PATENT DOCUMENTS

| | | | |
|---|---|---|---|
| JP | H11227725 | 8/1999 | |
| JP | 7563341 B2 * | 10/2024 | ............. B65B 55/24 |
| WO | 2025029550 | 2/2025 | |

OTHER PUBLICATIONS

"International Application Serial No. PCT US2024 039329, International Search Report mailed Dec. 6, 2024", 4 pgs.

(Continued)

*Primary Examiner* — Nicolas A Arnett

(74) *Attorney, Agent, or Firm* — SCHWEGMAN LUNDBERG & WOESSNER, P.A.

(57) ABSTRACT

A sterile filling method for an additive product container defining a product chamber adapted for containing an additive product can include forcing a first gas at a first temperature into the product chamber over a first threshold period to heat the product chamber to a first threshold temperature, such as to sterilize the product chamber. The sterile filling method can further include dispensing the additive product at a second temperature into the product chamber, sealing the product chamber; and, rotating the additive product container from a first position to a second position, such as to bring the additive product into contact with a sealing member sealing the product chamber.

15 Claims, 7 Drawing Sheets

(56) References Cited

U.S. PATENT DOCUMENTS

| | | | | | |
|---|---|---|---|---|---|
| 4,409,775 | A * | 10/1983 | Brody | B67C 7/0073 | 426/399 |
| 5,558,135 | A * | 9/1996 | Kronseder | B67C 3/10 | 141/39 |
| 5,860,461 | A * | 1/1999 | Helmut | B65B 51/142 | 53/426 |
| 7,886,899 | B2 * | 2/2011 | Frutin | B65D 51/2892 | 426/115 |
| 9,045,269 | B2 * | 6/2015 | Frutin | B65D 51/2864 | |
| 9,902,538 | B2 * | 2/2018 | Presche | B29C 45/14467 | |
| 10,472,142 | B2 * | 11/2019 | Presche | B65D 51/2892 | |
| 10,604,313 | B2 * | 3/2020 | Presche | B65D 51/2835 | |
| 10,773,868 | B2 * | 9/2020 | Maguire | B65D 51/2864 | |
| 10,899,515 | B2 * | 1/2021 | Maguire | B65D 43/0231 | |
| 11,001,425 | B2 * | 5/2021 | Maguire | B01F 25/28 | |
| 11,167,895 | B2 * | 11/2021 | Maguire | B65D 41/3447 | |
| 11,198,547 | B2 * | 12/2021 | Maguire | B65D 51/2892 | |
| 11,365,036 | B2 * | 6/2022 | Maguire | B65D 51/2892 | |
| 2011/0209796 | A1 * | 9/2011 | Feilner | B65B 3/06 | 222/145.5 |
| 2014/0311095 | A1 * | 10/2014 | Hayakawa | A61L 2/208 | 53/167 |
| 2017/0341791 | A1 * | 11/2017 | Weiler | B65B 55/027 | |
| 2019/0239542 | A1 * | 8/2019 | Trautwein | B65B 55/14 | |
| 2019/0298874 | A1 * | 10/2019 | Akiyama | B29C 49/46 | |
| 2024/0000124 | A1 * | 1/2024 | Chen | A23C 9/1542 | |

OTHER PUBLICATIONS

"International Application Serial No. PCT US2024 039329, Written Opinion mailed Dec. 6, 2024", 5 pgs.

* cited by examiner

STERILE FILLING METHOD FOR ADDITIVE PRODUCT CONTAINERS

TECHNICAL FIELD

This document pertains generally, but not by way of limitation, to methods or techniques for commercial sterile processing and packaging of liquid beverage products.

BACKGROUND

During the packaging of various consumable liquid products (e.g., liquid food or beverages), the liquid product itself, and the liquid container in which the liquid product will be packaged and sold, must be sterilized in accordance with one or more sterile packaging regulations, standards, or requirements. Several different types of sterile packaging techniques are currently in widespread use, such as, but not limited to, aseptic filling processes, cold filling processes, and hot filling processes. Aseptic filling processes and cold filling processes involve thermally sterilizing the liquid product, such as through heating or cooling of the liquid product, and chemically sterilizing the liquid container, such as through exposing the liquid container to an antiseptic chemical. In contrast, bot filling processes involve thermally sterilizing both the liquid product and the liquid container.

Figure 1:
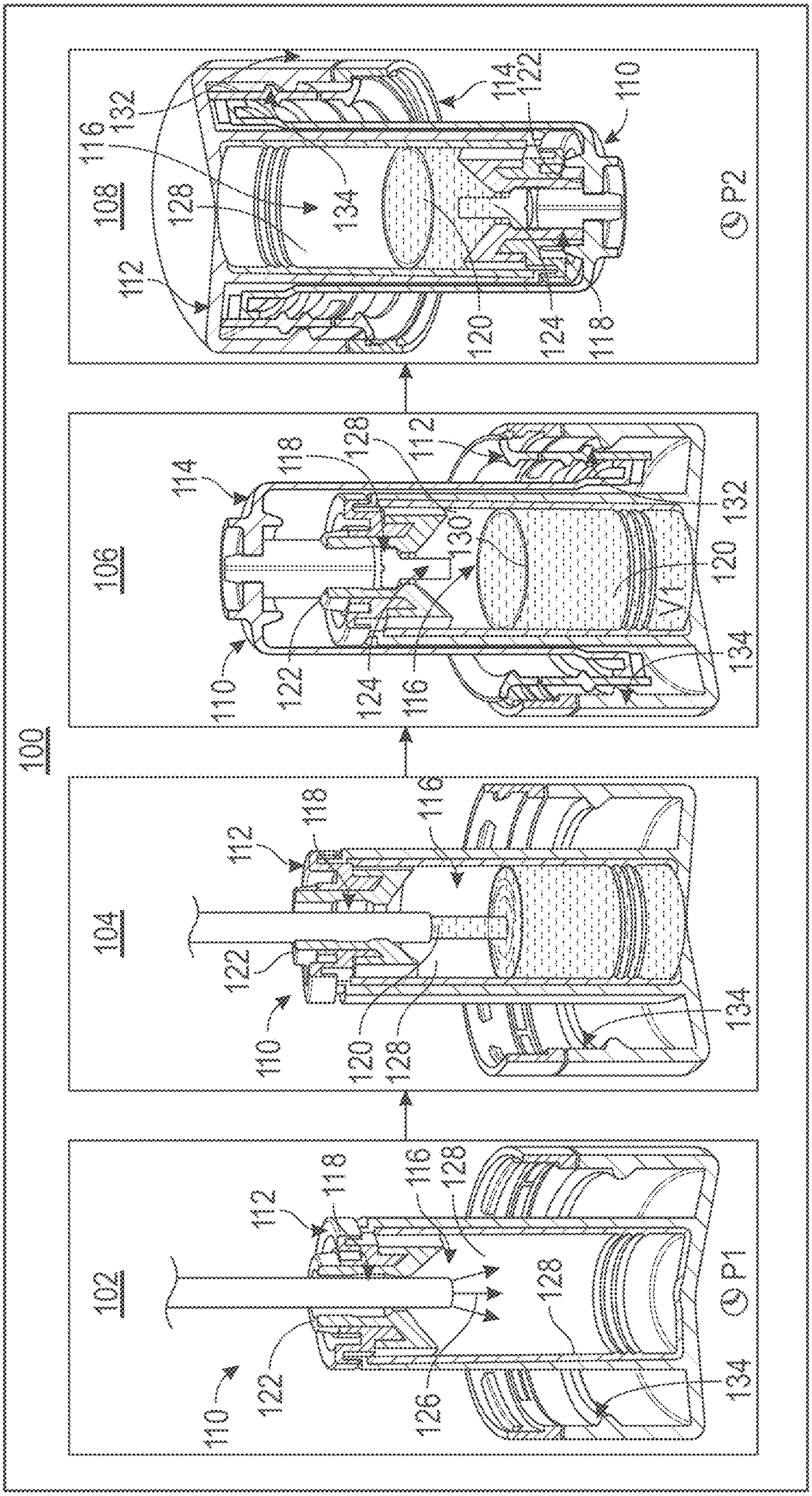
FIG. 1 illustrates an example sterile filling method, in accordance with one or more embodiments of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Hot filling processes can be used to efficiently sterilize a wide variety of different beverage products and containers, provide a long shelf life without refrigeration, can often be performed at lower cost than aseptic filling or cold filling processes, can avoid the use of antiseptic chemicals or artificial preservatives, and are commonly available at commercial co-packaging companies. As stated above, hot filling processes involve thermally sterilizing both liquid products and the liquid containers. For example, during a hot filling process, a liquid beverage product is first heated to predetermined temperature that is sufficient to sterilize the liquid product. Next, the heated liquid beverage product is dispensed into a liquid container at the predetermined temperature to, in turn; sterilize the liquid container through timewise exposure to the heated liquid beverage product. The predetermined temperature is carefully selected to ensure that the liquid beverage product will maintain an inner surface area of the liquid container in contact with the liquid beverage product at or above a minimum temperature for a minimum length of time, to thereby sterilize the liquid container in accordance with one or more sterile packaging regulations, standards, or requirements.

However, while the predetermined temperature can be increased or decreased based on various factors, such as the volume of a product to be packaged, the size, shape, of the material of a product container, or any applicable packaging requirements, sterilizing a product container using only a heated beverage product can be difficult or impossible in some packaging applications. For example, when a relatively low volume of product is being packaged, the surface area of a product container can be too large, relative to the volume of product, to be sterilized with the product alone, as the product will cool before the inner surface area of the product container is sterilized. Moreover, the predetermined temperature is often limited by a risk of damage to the product or the product container, which can prevent the predetermined temperature from being significantly increased to help address this issue. As a result, in many such applications, a product container can require sterilization before filling via another process, such as a wet or dry antiseptic treatment. As can be appreciated, this can significantly increase the cost and complexity of the hot filling process. In view of the above, a need exists for an improved bot filling process for relatively low product volume sterile packaging applications. However, the embodiments described herein may be used for all volumes of packaging applications, and as such, are not limited to low product volume packaging applications.

The present disclosure can help to address the above issues, among others, such as by providing a sterile filling method for, for example, a low product volume additive product container, such as an additive product container adapted for sealing, and bolding an additive product for introduction to, a product container. For example, in general, the sterile filling method can first include forcing a first gas at a first temperature, such as sterilized air, into the additive product container over a first threshold period to sterilize an inner surface area of the additive product container. The additive product can then be dispensed into the product chamber at a second temperature, and the product chamber can subsequently be sealed and, in some examples, pressurized.

The additive product container can then be optionally rotated to bring the sealing member into contact with the additive product, and maintained in position for a second threshold period until the sealing member is additionally sterilized through contact with the additive product. In view of the above, the sterile filling method of the present disclosure can provide an efficient technique for thermally sterilizing, for example, a low product volume additive product container, such as to thereby avoid the additional cost and complexity associated with a chemical sterilization process, or the risk of product damage associated with significantly increasing the temperature of an additive product.

FIG. 1 illustrates a pictographic flow chart of an example sterile filling method 100, in accordance with one or more embodiments of the present disclosure. In one or more examples, such as illustrated in FIG. 1, the sterile filling method 100 can include a first stage 102, a second stage 104, a third stage 106, and a fourth stage 108. The sterile filling method 100 is generally discussed herein with reference to cross-section views of an additive product container 110, such as shown in FIG. 1. However, it is to be appreciated that the sterile filling method 100 discussed herein can be applicable to a wide variety of different product containers adapted for holding products, or additive products for introduction into the products, therein, such as, but not limited to, cans or bottles made from various materials. The additive product container 110 shown in FIG. 1 can be generally representative of any of the container closures or additive product containers disclosed, for example, in U.S. Pat. Nos. 7,886,899, 9,045,269, 9,902,538, 10,472,142, 10,604,313, 10,773,868, 10,899,515, 11,001,425, 11,167,895, 11,198,547, 11,167,895, 11,365,036, each of which is herein incorporated by reference in its entirety.

In some examples, the additive product container 110 can include a cap member 112 and a housing 114. The cap member 112 can generally be a three-dimensional body member sized and shaped to define a product chamber 116. In some examples, such as shown in FIGS. 1-S, the cap member 112 can be a container cap adapted for closing or otherwise engaging with a liquid beverage container. The cap member 112 can define a product chamber 116 and a fluid passage 118. The product chamber 116 can be adapted to hold an additive product 120. In some examples, the additive product 120 can be an additive liquid for mixing with a second liquid product, such as, but not limited to, at the time of, or in preparation for, user consumption. In other examples, the additive product 120 can be a powder or otherwise dry additive for mixing with a liquid product, such as, but not limited to, at the time of, or in preparation for, user consumption. The fluid passage 118 can extend within the cap member 112, such as between the product chamber 116 and a lower end surface 122.

The housing 114 can generally be a three-dimensional body member sized and shaped to seal, or otherwise close, the product chamber 116. In some examples, the housing 114 can include a sealing member 124. The sealing member 124 can be adapted to seal the additive product 120 within the product chamber 116 of the additive product container 110, such as by, but not limited to, establishing a fluid or air tight seal between the cap member 112 and the housing 114 within the fluid passage 118. In some examples, such as shown in FIGS. 1-4, the housing 114 can be adapted for closing or otherwise engaging with a liquid beverage container. In further examples, the additive product container 110 may not include the housing 114, and may only include the cap member 112 and the sealing member 124. In one or more examples, the sealing member 124 may be made from a material that is different from the cap member 112 or the housing 114, such as, but not limited to, rubber or an elastomeric material, or a paper or foil material.

The sterile filling method 100 can begin with the first stage 102. The first stage 102 can include forcing a first gas 126 at a first temperature, such as, but not limited to, sterilized air, nitrogen, or other inert gasses, into the product chamber 116 over a first threshold period P1. The first threshold period P1 can be a length of time during which the first gas 126, at the first temperature, is continuously forced into the product chamber 116 at a constant flow rate. The first threshold period P1 and the first temperature can collectively be configured to ensure that an inner surface area 128, including the product chamber 116 and the fluid passage 118, is sterilized in accordance with one or more applicable packaging standards, regulations, or requirements. For example, during the first threshold period P1, the inner surface area 128 can be heated to, and be maintained at, a desired or required temperature, such as, but not limited to, a temperature of about 80 degrees Celsius. In one such example, the first threshold period P1 may be about 20 seconds. In this way, all surfaces (e.g., the inner surface area 128) of the cap member 112 that can contact the additive product 120 can be effectively sanitized during the first stage 102.

Next, the sterile filling method 100 can proceed to the second stage 104. The second stage 104 can include dispensing the additive product 120 at a second temperature into the product chamber 116. The second temperature can be a temperature equal to or greater than a temperature sufficient to ensure that the additive product 120 is sterilized in accordance with one or more applicable packaging standards, regulations, or requirements. For example, the second temperature can be within any temperature range used by other hot filling processes, such as, but not limited to, between about 84 degrees Celsius and about 95 degrees Celsius. After the product chamber 116 has been filled with the additive product 120, the sterile filling method 100 can proceed to the third stage 106.

The third stage 106 can include sealing the product chamber 116 of the additive product container 110. For example, during the third stage 106, the sealing member 124 of the housing 114, which in one example may be provided in the form of a plug member, can be inserted into the fluid passage 118 until a first detent means 132 of the housing 114 engages a second detent means 134 of the cap member 112, to concurrently couple the housing 114 to the cap member 112 and establish a fluid tight seal between the product chamber 116 and the lower end surface 122. In other examples, the housing 114 can be may be screwed, snapped, adhered, or otherwise secured to the cap member 112 to seal the product chamber 116. In still further examples, such as in examples where the additive product container 110 does not include the housing 114, the sealing member 124 can be inserted into, coupled to, or otherwise positioned on or within the cap member 116 to seal the product chamber 116. Subsequently, during the third stage 106, the product chamber 116 can optionally be pressurized, such as to help extend the shelf life of the additive product 120. For example, the product chamber 116 can be pressurized in a manner similar or different to as described in U.S. Pat. Nos. 7,886,899, 9,045,269, 9,902,538, 10,472, 142, 10,604,313, 10,773,868, 10,899,515, 11,001,425, 11,167,895, 11,198,547, 11,167,895, 11,365,036, each of which is herein incorporated by reference in its entirety. Finally, the sterile filling method 100 can optionally proceed to the fourth stage 108.

The fourth stage 108 can include rotating the additive product container 110 from a first position to a second position. For example, during the fourth stage 108, the additive product container 110 can be rotated about 180 degrees around a first axis A1 (FIG. 5) defined by the additive product container 110. In some examples, as the additive product container 110 rotates from the first position to the second position, the additive product 120 can shift within the product chamber 116 and at least partially surround the sealing member 124. The additive product container 110 can then be maintained in the second position for a second threshold period P2 to sanitize the sealing member 124 in accordance with one or more applicable packaging standards, regulations, or requirements. For example, during the second threshold period P2, the sealing member 124 can be heated to, and be maintained at, a desired temperature, such as, but not limited to, a temperature of about 80 degrees Celsius. In one such example, the second threshold period P2 may be about 20 seconds.

In view of all the above, the sterile filling method 100 can enable both the additive product 120, and the additive product container 110, to be efficiently sterilized without exposing the additive product container 110 to aseptic chemicals, or significantly increasing the temperature of the additive product 120 beyond a standard, or minimum, temperature range commonly used to sterilize the additive product 120. The sterile filling method 100 can thereby help to reduce the cost and complexity of, and reduce the risk of product damage in, hot filling processes.

Figure 2:
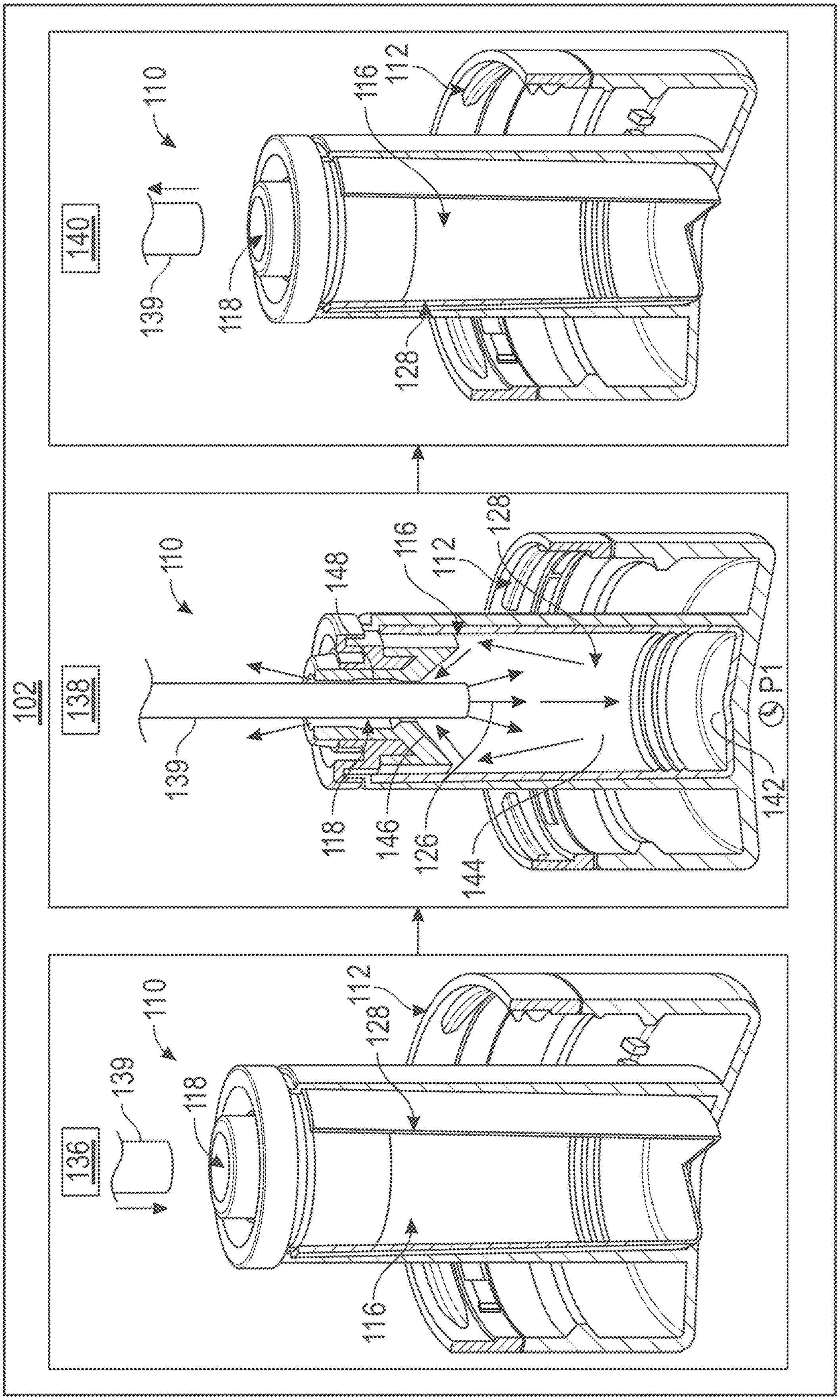
FIG. 2 illustrates an example first stage of the sterile filling method of FIG. 1, in accordance with one or more embodiments of the present disclosure.

FIG. 2 illustrates an example first stage 102 of the sterile filling method 100 of FIG. 1, in accordance with one or more embodiments of the present disclosure. The first stage 102 can, in one or more examples, include a first operation 136, a second operation 138, and a third operation 140, such as shown in FIG. 2. The first operation 136 can include positioning the cap member 112 in, for example, but not limited to, an inverted position, and inserting a first nozzle 139 through the fluid passage 118 until the first nozzle 139 enters, and is at least partially received within, the product chamber 116 of the cap member 112. The first nozzle 139 can be a syringe, or otherwise a generally tubular or tapered instrument of manual or automated means for heating and forcing (e.g., blowing) the first gas 126 into the product chamber 116.

Once the first nozzle 139 is located at least partially within the product chamber 116, the first stage 102 can proceed to the second operation 138. The second operation 138 can include forcing the first gas 126 through the first nozzle 139 at the first temperature, over the first threshold period P1, to heat the inner surface area 128 to the first threshold temperature. For example, during the second operation 138, the first gas 126 can continuously flow out of the first nozzle 139 within the product chamber 116 to, in turn, contact and beat all inner surfaces of the product chamber 116, such as a first surface 142, a second surface 144, and a third surface 146, to the first threshold temperature; and, continuously flow out of the product chamber 116 through the fluid passage 118 to, in turn, contact and heat the inner surface thereof (i.e., fourth surface 148) to the first threshold temperature. Finally, after the inner surface area 128 has been heated to the first threshold temperature during the second operation 138, the first stage 102 can proceed to the third operation 140. The third operation 140 can include withdrawing the first nozzle 139 from the product chamber 116, such as until the first nozzle 139 is entirely removed from the fluid passage 118.

As can be appreciated, each variable of the first stage 102 of the sterile filling method 100 can depend, or otherwise be based on, one another or one or more variables of the second stage 104 (FIGS. 1 & 3), the third stage 106 (FIGS. 1 & 4), or the fourth stage 108 (FIGS. 1 & 5), to ensure that the inner surface area 128 is both thermally sterilized and heated sufficiently to prevent the additive product 120 from falling below a desired or required temperature during the second threshold period P2 (FIGS. 1 & 5) of the fourth stage 108 of the sterile filling method 100. For example, variables such as the first threshold period P1, the first temperature, and a flow rate at which the first gas 126 flows through the product chamber 116 over the first threshold period P1, can be collectively configured (e.g., varied) based on various factors or variables such as, but not limited to: (1) the material or a material property of the additive product container 110 or the additive product 120 (FIG. 1), (2) the total volume of the product chamber 116, (3) a volume V1 (FIGS. 1 & 3-4) of the additive product 120 (FIGS. 1 & 3-4), (4) the second temperature at which the additive product 120 is dispensed into the product chamber 116 during the second stage 104, (5) a diameter of the first nozzle 139 or the fluid passage 118. (6) a pressure at which the product chamber 116 is to be pressurized, and (7) a length of time between the second operation 138 and the second stage 104, the third stage 106, or the fourth stage 108.

In one or more examples, the material of the cap member 112 or the housing 114 of the additive product container 110 can be, for example, but not limited to, polyetheretherketone ("PEEK"), aluminum, glass, Polyethylene terephthalate ("PET"), Polybutylene terephthalate ("PBT"). Polypropylene ("PP"), plastic alternative resins, post-consumer recycled resin, seaweed resin, potato resin, or other materials. In one or more examples, the total volume of the product chamber 116 can be, for example, but not limited to, between about 3 milliliters and 20 milliliters, between about 21 milliliters and about 50 milliliters, between about 51 milliliters and about 100 milliliters, and between about 101 milliliters and 10 liters. In one or more examples, the volume V1 of the additive product can be, for example, but not limited to, between about 3 milliliters and 20 milliliters, between about 21 milliliters and about 50 milliliters, between about 51 milliliters and about 100 milliliters, and between about 101 milliliters and 10 liters. In one or more examples, the second temperature at which the additive product 120 is dispensed into the product chamber 116 during the second stage 104 can be, but is not limited to, between about 84 degrees Celsius and about 95 degrees Celsius.

In one or more examples, the pressure at which the product chamber 116 can be optionally pressurized can be, for example, but not limited to, between 100 pounds per square inch and about 120 pounds per square inch. In one or more examples, the length of time between the second operation 138 and the second stage 104 can be, for example, but is not limited to, between about 1 second and about 8 seconds. In one or more examples, the length of time between the second operation 138 and the third stage 106 can be, for example, but is not limited to, between about 10 seconds and about 15 seconds. In one or more examples, the length of time between the second operation 138 and the third stage 106 can be, for example, but is not limited to, between about 22 seconds and about 52 seconds.

In any of the above examples, the first threshold period P1 can be, for example, but not limited to, between about 45 seconds and about 50 seconds. In any of the above examples, the first temperature can be, for example, but not limited to, between about 153 degrees Celsius and about 157 degrees Celsius. In any of the above examples, the first threshold temperature can be, for example, but is not limited to, 139 degrees Celsius and about 141 degrees Celsius. In any of the above examples, the flow rate at which the first gas 126 flows through the product chamber 116 over the first threshold period P1 can be, for example, but is not limited to, about 0.2 cubic feet per minute and about 1 cubic feet per minute, or between about 0.5 cubic feet per minute and about 0.8 cubic feet per minute. Additionally, as can be appreciated, the pressure within the product chamber 116 can drop, or decrease, in proportion to the flow rate which the first gas 126 flows through the product chamber 116 during the second operation 138. In one or more examples, the pressure within the product chamber 116 during the second operation 138 can be, but is not limited to, about 0.5 pounds per square inch and about 2 pounds per square inch.

In one example, the volume V1 can be about 30 milliliters, the second temperature at which the additive product 120 is dispensed into the product chamber 116 during the second stage 104 can be about 84 degrees Celsius, the pressure at which the product chamber 116 is to be pressurized can be about 110 pounds per square inch, and the length of time between the second operation 138 of the first stage 102 and the fourth stage 108 can be between about 22 seconds and about 52 seconds. In such an example, the first threshold period P1 can be about 45 seconds, the first temperature can be between about 155 degrees Celsius, and the flow rate at which the first gas 126 is forced into the product chamber 116 can be, but is not limited to, about 0.5 cubic feet per minute, and a pressure within the product chamber can be about, but is not limited to, about 1 pound per square inch.

Figure 3:
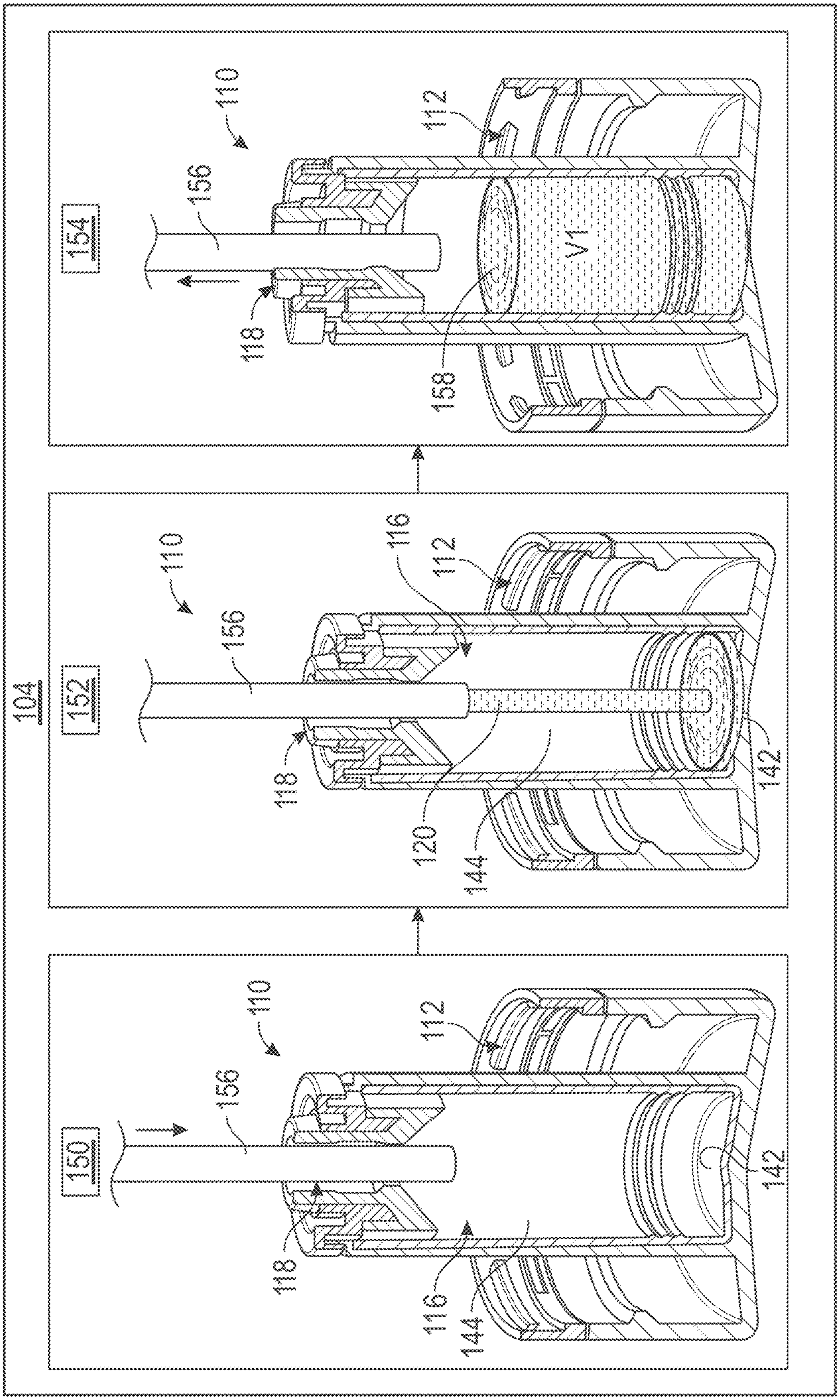
FIG. 3 illustrates an example of a second stage of the sterile filling method of FIG. 1, in accordance with one or more embodiments of the present disclosure.

FIG. 3 illustrates an example of a second stage 104 of the sterile filling method 100 of FIG. 1, in accordance with one or more embodiments of the present disclosure. In one or more examples, the second stage 104 can include a first operation 150, a second operation 152, and a third operation 154, such as shown in FIG. 3. In some examples, the first operation 150 can include inserting a second nozzle 156 through the fluid passage 118 until the second nozzle 156 enters, and is at least partially received within, the product chamber 116 of the cap member 112, such as, but not limited to, in an example where the additive product 120 is a liquid or a powder. The second nozzle 156 can be a syringe, or otherwise a generally tubular or tapered instrument of manual or automated means for filling the product chamber 116 with the additive product 120. In some examples, only one nozzle may be used. For example, only the first nozzle 139 can be used for various operations of the first stage 102 (FIGS. 1-2) and the second stage 104. Once the second nozzle 156 is located at least partially within the product chamber 116, the second stage 104 can proceed to the second operation 152.

The second operation 152 can include dispensing the additive product 120 at the second temperature into the product chamber 116. For example, during the second operation 152, the additive product 120 can flow out of the second nozzle 156 within the product chamber 116 to, in turn, contact the first surface 142 and the second surface 144 each heated to the first threshold temperature during the first stage 102 (FIGS. 1-2). As such, during the second operation 152, the first surface 142 and the second surface 144 of the inner surface area 128 can be at a temperature that is greater than the second temperature at which the additive product is added into the product chamber 116. This can cause the additive product 120 to increase in temperature or at least maintain temperature longer, and, as such, help to prevent the additive product 120 from cooling significantly during the second stage 104. Accordingly, by virtue of forced gas heating of the inner surface area 128 during the first stage 102, the first surface 142 and the second surface 144 can help additive product 120 from falling below a desired or required temperature during the second threshold period P2 (FIGS. 1 & 5) of the fourth stage 108 (FIGS. 1 & 4).

During the second operation 152, the additive product 120 can continue to flow through the second nozzle 156 until a volume V1 has been dispensed, or otherwise added, into the product chamber 116. In one or more examples, the volume V1 can represent a volume of fluid that is between about, but not limited to, 100 percent and about 40 percent of a total volume of the product chamber 116. After the volume V1 has been dispensed into the product chamber 116 during the second operation 138, the second stage 104 can proceed to the third operation 154. The third operation 154 can include withdrawing the second nozzle 156 from the product chamber 116, such as until the second nozzle 156 is entirely removed from the fluid passage 118. In one or more examples, the third operation 154 can also include verifying the volume V1. For example, the third operation 154 can include weighing the cap member 112, such as by positioning the cap member 112 to confirm that a weight of the cap member 112 is within a weight range associated with the cap member 112 when the product chamber 116 is filled with the first volume V1.

Figure 4:
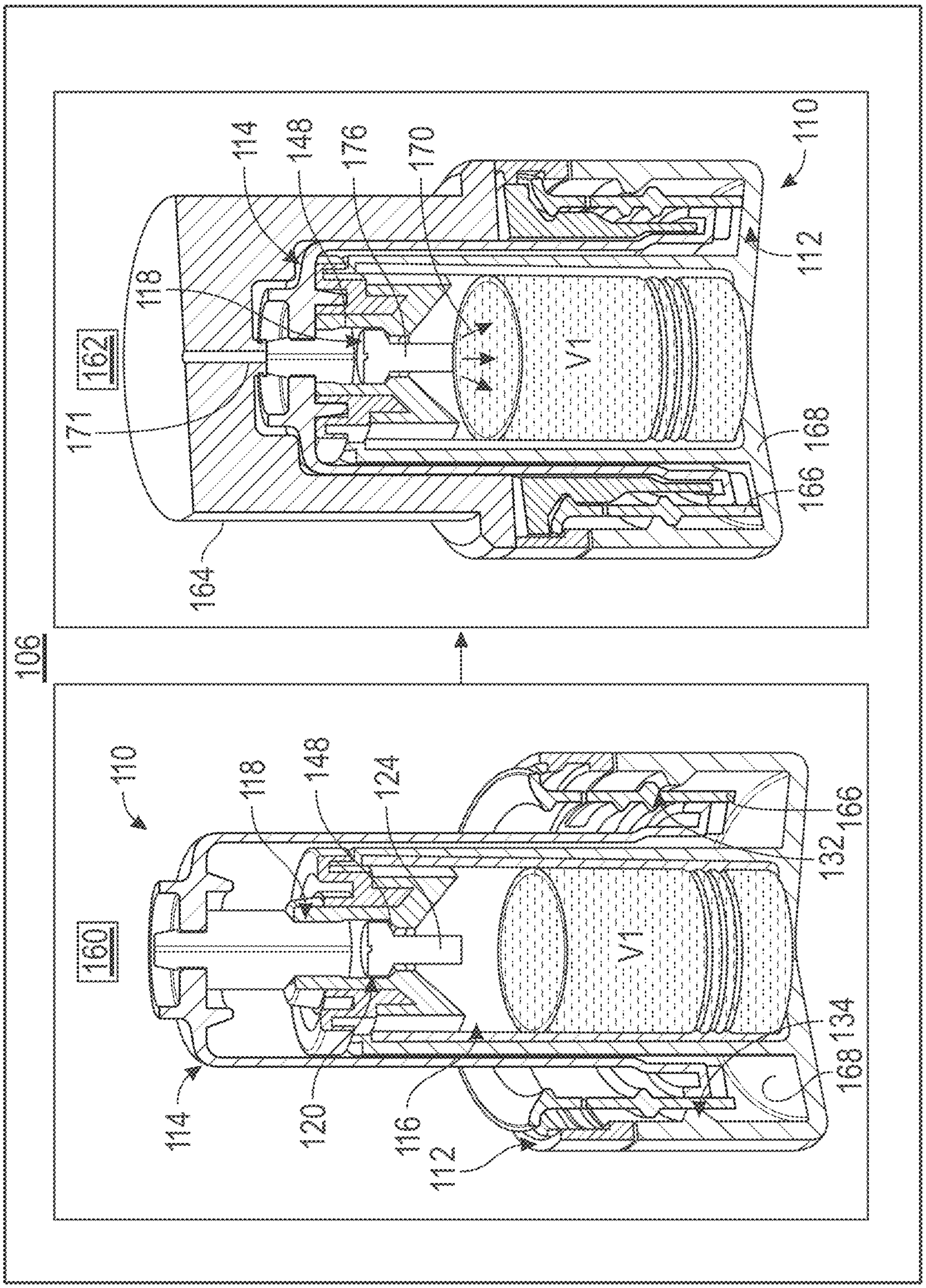
FIG. 4 illustrates an example third stage of the sterile filling method of FIG. 1, in accordance with one or more embodiments of the present disclosure.

FIG. 4 illustrates an example third stage 106 of the sterile filling method 100 of FIG. 1, in accordance with one or more embodiments of the present disclosure. The third stage 106 can include sealing the product chamber 116 of the cap member 112. In one or more examples, sealing the product chamber 116 can include a first operation 160 and an optional second operation 162, such as shown in FIG. 4. The first operation 160 can include establishing a fluid tight seal between the product chamber 116 and the housing 114. For example, under downward pressure from a sealing adapter 164, the sealing member 124 of the housing 114 can slide along the fourth surface 148 within the fluid passage 118 until the sealing member 124 enters the product chamber 116, and the housing 114 is fully seated within the cap member 112. The housing 114 can be fully seated in the cap member 112 when a first contacting surface 166 of the housing 114 engages a second contacting surface 168 of the cap member 112. In other examples, the housing 114 can alternatively be screwed, snapped, adhered, pressed, or otherwise secured to the cap member 112 to cause the sealing member 124 to seal the product chamber 116. In still further examples, the sealing member 124 alone can be secured to the cap member 112 to seal the product chamber 116, such an in examples where the additive product container 110 does not include the housing 114.

In some examples, the first operation 160 can include coupling the housing 114 to the cap member 112. For example, as the sealing member 124 of the housing 114 slides along the fourth surface 148 within the fluid passage 118 under downward pressure from the sealing adapter 164, the first detent means 132 of the housing 114 can slide along, and subsequently over, the second detent means 134 of the cap member 112 to lock, or otherwise secure, the housing 114 to the cap member 112. In such an example, the sealing adapter 164 can generally be a socket, an end effector, or any other device of a manual or automated means for driving (e.g., pressing) the housing 114 into the cap member 112 and, in some examples, forcing a second gas 170 into the product chamber 116.

The third stage 106 can optionally include the second operation 162. The second operation 162 can include pressurizing the product chamber 116. For example, during the second operation 162, the second gas 170 can be forced through a lumen 171, defined by the sealing adapter 164, in one-way fluid communication with the product chamber 116. Such one-way fluid communication can be enabled, or otherwise established, by one or more features of the sealing member 124 and the fourth surface 148 of the cap member 112. In one or more examples, the product chamber 116 can be pressurized during the second operation 162 to a pressure of between 100 pounds per square inch and about 120 pounds per square inch. In one example, the product chamber 116 can be pressurized during the second operation 162 to a pressure equal to, or greater than, 110 pounds per square inch.

Figure 5:
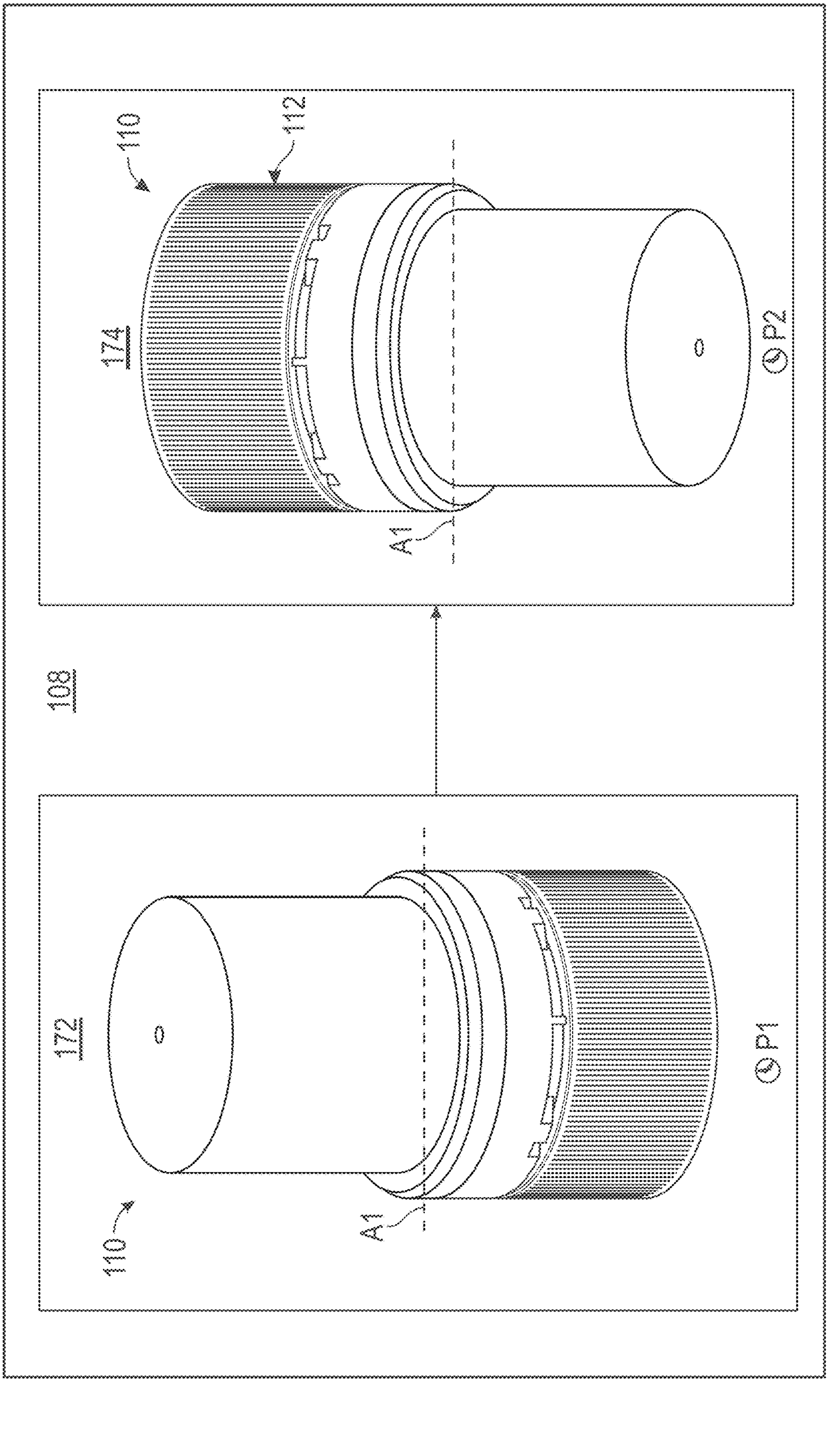
FIG. 5 illustrates an example fourth stage of the sterile filling method of FIG. 1, in accordance with one or more embodiments of the present disclosure.

FIG. 5 illustrates an example optional fourth stage 108 of the sterile filling method 100 of FIG. 1, in accordance with one or more embodiments of the present disclosure. Also illustrated in FIG. 5 is a first axis A1 defined by the additive product container 110. The first axis A1 can be lateral axis A1 of the additive product container 110. The fourth stage 108 can include rotating the additive product container 110 from a first position 172 to a second position 174. For example, during the fourth stage 108, the additive product container 110 can be rotated about 180 degrees around the first axis A1. In such an example, the first position 172 can generally be an inverted orientation and the second position 174 can generally be an upright orientation.

Once the additive product container 110 is in the second position 174, the volume V1 (FIGS. 3-4) of the additive product 120 can shift within the product chamber 116 to at least partially surround the sealing member 124 therein, such as shown in FIG. 1. Next, the additive product container 110 can be maintained in the second position 174 for the second threshold period P2 to sterilize an outer surface area 176 of the sealing member 124 in accordance with one or more applicable packaging standards, regulations, or requirements. For example, during the second threshold period P2, the sealing member 124 can be heated to, and be maintained at, a desired or required temperature, such as, but not limited to, a temperature of about 80 degrees Celsius. The second threshold period P2 may be about 20 seconds.

In view of all the above, the first stage 102 (FIGS. 1-2) can enable the additive product 120 to sanitize the sealing member 124, such as in accordance with one or more sterile packaging standards, regulations, or requirement, during the fourth stage 108. For example, by virtue of continuous contact, during the second stage 104 and the third stage 106, with the inner surface area 128 heated to the first threshold temperature during the first stage 102, the additive product 120 can remain at or above a desired or required temperature for a desired time interval (e.g., the second threshold period P2) to sanitize a variety of additive products, such as, but not limited to, at or above 80 degrees Celsius for a time interval of at least 20 seconds. In this way, all surfaces of the housing 114 that can contact the additive product 120 (e.g., the outer surface area 176 of the sealing member 124) can be effectively sanitized during the fourth stage 108 of the sterile filling method 100.

Figure 6:
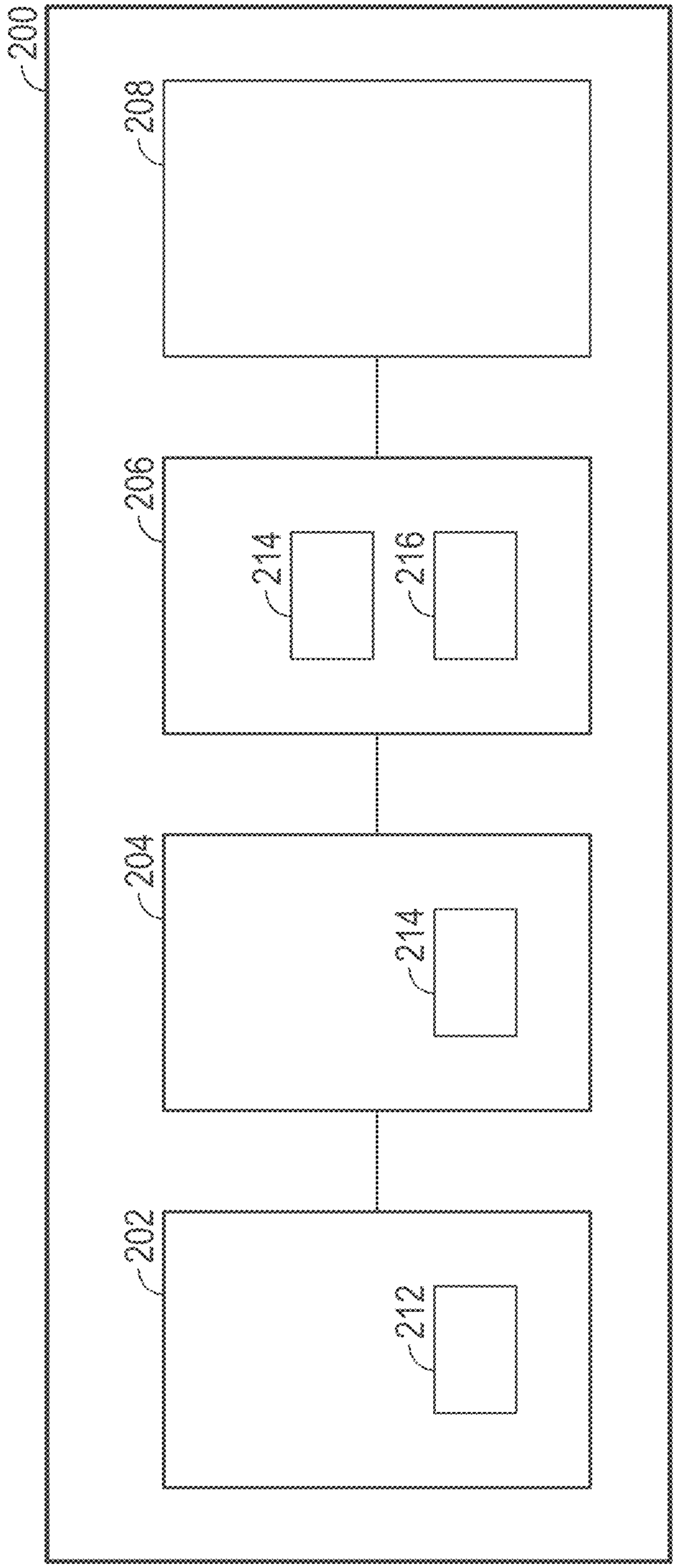
FIG. 6 illustrates an example sterile filling system for performing the sterile filling method of FIGS. 1-6, in accordance with one or more embodiments of the present disclosure.

FIG. 6 illustrates an example sterile filling system 200 for performing the sterile filling method 100 of FIGS. 1-5, in accordance with one or more embodiments of the present disclosure. As such, FIG. 6 is discussed with reference to FIGS. 1-S above. The sterile filling system 200 can include a first station 202. The first station 202 can be adapted for forcing the first gas 126 at the first temperature into the product chamber 116 (FIGS. 1-4) over the first threshold period P1 (FIGS. 1-2) to heat the product chamber 116 to a first threshold temperature.

For example, the first station 202 can include manually operated or automated means, such as one or more manually operated machines or devices, or one or more computer-controlled/robotic systems, respectively, or any combination thereof, configured to automatically perform any of the steps or operations discussed with reference to the first stage 102 (FIGS. 1-2). In one or more examples, the first station 202 can include a heating system 212. The heating system 212 can include the first nozzle 139 (FIG. 2) and be adapted to beat the first gas 126 to the first temperature and force the first gas 126 through the first nozzle 139 at a continuous flow rate.

The sterile filling system 200 can include a second station 204. The second station 204 can be adapted for dispensing the additive product 120 (FIGS. 1 & 3-4) at the second temperature into the product chamber 116 (FIG. 1-4). For example, the second station 204 can include manual or automated means, such as one or more manually operated machines or devices, or one or more computer-controlled/robotic systems, respectively, or any combination thereof, configured to perform any of the steps or operations discussed with reference to the second stage 104 (FIGS. 1 & 3). In one or more examples, the second station 204 can include a dispensing system 214. The dispensing system 214 can include the second nozzle 156 (FIG. 3) and can be adapted to heat the additive product 120 (FIGS. 1-4) to the second temperature and dispense the volume V1 (FIG. 3) of the additive product 120 through the second nozzle 156.

The sterile filling system 200 can include a third station 206. The third station 206 can be adapted for sealing the product chamber 116 of the additive product container 110. For example, the second station 204 can include manual or automated means, such as, but not limited to, one or more manually operated machines or devices, or one or more computer-controlled/robotic systems, or any combination thereof, configured to perform any of the steps or operations discussed with reference to the third stage 106. In one or more examples, the third station 206 can include a pressing system 216 and a gassing system 218. The pressing system 216 can include the sealing adapter 164 (FIG. 4) and can be adapted to drive the housing 114 (FIGS. 1-5) of the additive product container 110 onto, or otherwise into engagement with, the cap member 112 (FIGS. 1-5) of the additive product container 110 to seal the product chamber 116 of the additive product container 110. The gassing system 218 can be a system of, or can otherwise be in fluid communication with, the pressing system 216 and can be adapted to force the second gas 170 (FIG. 4) into the product chamber 116 to pressurize the product chamber 116.

The sterile filling system 200 can include a fourth station 208. The fourth station 208 can be adapted to rotate the additive product container 110 from a first position (FIG. 5) to a second position (FIG. 5). For example, the fourth station 208 can include manual or automated means, such as, but not limited to, one or more manually operated machines or devices, or one or more computer-controlled/robotic systems, or any combination thereof, configured to perform the fourth stage 108 (FIG. 5) of the sterile filling method 100 (FIG. 1). In one or more examples, two or more of the first station 202, the second station 204, the third station 206, or the fourth station 208, or any of various operations thereof, can be combined in a single station.

Figure 7:
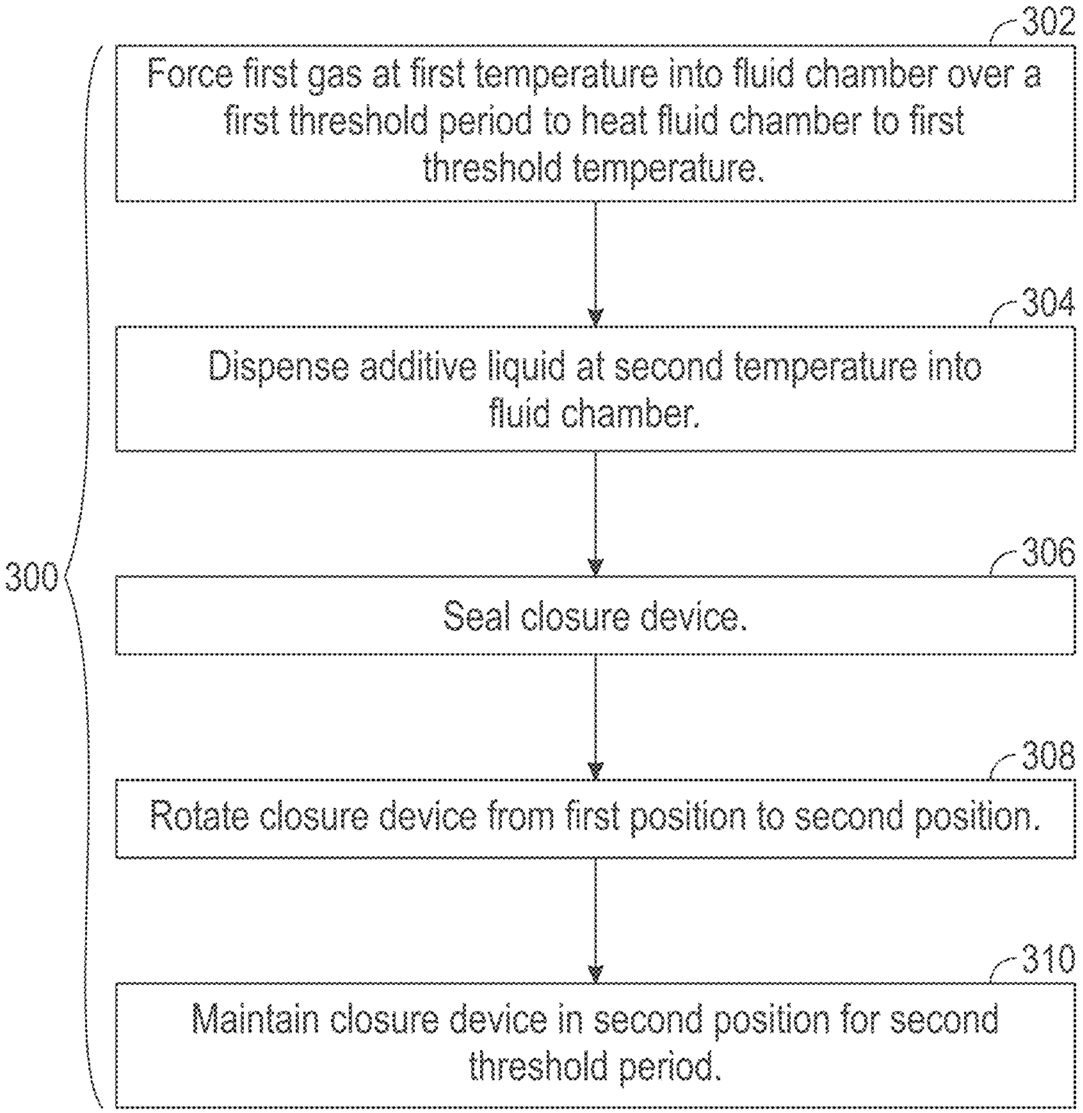
FIG. 7 illustrates a flow chart of an example sterile filling method, in accordance with one or more embodiments of the present disclosure.

FIG. 7 illustrates a flow chart of an example sterile filling method 300, in accordance with one or more embodiments of the present disclosure. The steps or operations of the sterile filling method 300 are illustrated in a particular order for convenience and clarity; many of the discussed operations can be performed by multiple different actors, devices, or systems. It is understood that subsets of the operations discussed in the sterile filling method 300 can be attributable to a single actor, device, or system and can be considered a separate standalone process or method.

The sterile filling method 300 can include step 302. The step 302 can include forcing a first gas at a first temperature into the product chamber over a first threshold period to heat the product chamber to a first threshold temperature. For example, sterilized air heated to the first temperature can be continuously forced into the product chamber through a fluid passage of the additive product container during the first threshold period, such as until the inner surface of the additive product container reaches the first threshold temperature. The first threshold period and the first temperature can be collectively configured ensure that an inner surface of the cap member is sterilized in accordance with one or more applicable packaging standards, regulations, or requirements.

In one or more examples, the step 302 can include inserting a first nozzle into the product chamber. For example, the first nozzle can be inserted through a fluid passage of a cap member defining the product chamber until the first nozzle enters the product chamber. In one or more examples, the step 302 can include forcing the first gas into the product chamber at a flow rate greater than or equal to 0.5 cubic feet per minute.

The sterile filling method 300 can include step 304. The step 304 can include dispensing the additive product at a second temperature into the product chamber. For example, the additive product heated to the second temperature can be continuously added to the product chamber through a fluid passage of the additive product container, such as until a volume of additive product is received within the product chamber. The second temperature can be configured ensure the additive product is sterilized in accordance with one or more applicable packaging standards, regulations, or requirements. In one or more examples, the step 304 can include inserting a second nozzle into the product chamber. For example, the second nozzle can be inserted through a fluid passage of a cap member defining the product chamber until the second nozzle enters the product chamber.

The sterile filling method 300 can include step 306. The step 306 can include sealing the product chamber. For example, a housing of the additive product container can be coupled to a cap member of the additive product container to establish a fluid tight seal between the housing and product chamber of the cap member. In one or more examples, the step 306 can include inserting a sealing member into the product chamber to establish a fluid tight seal between the sealing member and the product chamber. For example, the sealing member can be inserted into a fluid passage of the cap member until a first detent means of the housing engages a second detent means of the cap member thereby to couple the housing member to the cap member and establish a fluid tight seal between the product chamber and the housing.

In one or more examples, the step 306 can include pressurizing the product chamber with a second gas. For example, the second gas can be forced through a lumen in one-way fluid communication with the product chamber.

The sterile filling method 300 can include step 308. The step 308 can include rotating the additive product container from a first position to a second position. For example, the additive product container can be inverted to cause additive fluid within a product chamber of a cap member of the additive product container to at least partially surround a sealing member of a housing of the additive product container in the additive fluid. In one or more examples, the step 308 can include rotating the additive product container between about 120 and 240 degrees, between about 150 and 210 degrees, or about 180 degrees. For example, the additive product container can be rotated about 180 around a first axis defined by the additive product container. However, any amount of rotation along any of one or more axes of the additive product container may be suitable and is contemplated by the present disclosure.

The sterile filling method 300 can optionally include step 310. The step 310 can include maintaining the additive product container in the second position for a second threshold period after rotating the additive product container from the first position to the second position. For example, the additive product container can be inverted, or rotated about 180 degrees around a first axis defined by the additive product container to cause additive fluid within a product chamber of a cap member of the additive product container to at least partially surround a sealing member of a housing of the additive product container in the additive fluid. The second threshold period can be configured ensure that an inner surface of the cap member is sterilized in accordance with one or more applicable packaging standards, regulations, or requirements.

The foregoing systems and devices, etc. are merely illustrative of the components, interconnections, communications, functions, etc. that can be employed in carrying out examples in accordance with this disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided.

Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B." unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third." etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

NOTES AND EXAMPLES

The following, non-limiting examples, detail certain aspects of the present subject matter to solve the challenges and provide the benefits discussed herein, among others.

Example 1 is a sterile filling method for an additive product container defining a product chamber adapted for containing an additive product, the sterile filling method comprising: forcing a first gas at a first temperature into the product chamber over a first threshold period to heat the product chamber to a first threshold temperature; dispensing the additive product at a second temperature into the product chamber; sealing the product chamber, and rotating the additive product container from a first position to a second position.

In Example 2, the subject matter of Example 1 includes, wherein forcing the first gas at the first temperature into the product chamber over the first threshold period includes forcing the first gas into the product chamber at a flow rate greater than or equal to 0.5 cubic feet per minute.

In Example 3, the subject matter of Examples 1-2 includes, wherein the first temperature is between about 153 degrees Celsius and about 157 degrees Celsius.

In Example 4, the subject matter of Example 3 includes, wherein the first threshold period is between about 45 seconds and about 50 seconds.

In Example 5, the subject matter of Example 4 includes, wherein the first threshold temperature is between about 139 degrees Celsius and about 141 degrees Celsius.

In Example 6, the subject matter of Example 5 includes, wherein the sterile filling method further comprises maintaining the additive product container in the second position for a second threshold period after rotating the additive product container from the first position to the second position.

In Example 7, the subject matter of Example 6 includes, wherein the second threshold period is at least about 20 seconds.

In Example 8, the subject matter of Example 7 includes, wherein the second temperature is between about 84 degrees Celsius and about 95 degrees Celsius.

In Example 9, the subject matter of Example 8 includes, wherein rotating the additive product container from the first position to the second position includes rotating the additive product container about 180 degrees.

In Example 10, the subject matter of Example 9 includes, wherein sealing the product chamber includes: inserting a sealing member into the product chamber to establish a fluid tight seal between the sealing member and product chamber.

In Example 11, the subject matter of Example 10 includes, wherein sealing the product chamber includes pressurizing the product chamber with a second gas.

In Example 12, the subject matter of Example 11 includes, wherein pressurizing the product chamber with the second gas includes pressurizing the product chamber to a pressure greater than or equal to 110 pounds per square inch.

In Example 13, the subject matter of Example 12 includes, wherein forcing the first gas at the first temperature into the product chamber includes inserting a first nozzle into the product chamber; and wherein dispensing the additive product at the second temperature includes inserting a second nozzle into the product chamber.

In Example 14, the subject matter of Example 13 includes, wherein dispensing the additive product at the second temperature into the product chamber includes weighing the cap member to verify a volume of the additive product within the product chamber.

Example 15 is a sterile filling system for an additive product container defining a product chamber adapted for containing an additive product, the sterile filling system comprising: a first station adapted for forcing a first gas at a first temperature into the product chamber over a first threshold period to heat the product chamber to a first threshold temperature; a second station adapted for dispensing the additive product at a second temperature into the product chamber; a third station adapted for sealing the product chamber of the additive product container; and a fourth station adapted for rotating the additive product container from a first position to a second position.

In Example 16, the subject matter of Example 15 includes, wherein the first station includes a first nozzle adapted for insertion into the product chamber to force the first gas there into.

In Example 17, the subject matter of Example 16 includes, wherein the first station includes a heating system adapted to heat the first gas to the first temperature and force the first gas through the first nozzle at a continuous flow rate.

In Example 18, the subject matter of Example 17 includes, wherein the station includes a second nozzle adapted for insertion into the product chamber to add the additive product there into.

In Example 19, the subject matter of Example 18 includes, wherein the second station includes a dispensing system adapted to heat the additive product to the second temperature and dispense a volume of the additive product through the second nozzle.

In Example 20, the subject matter of Examples 15-19 includes, wherein the third station includes: a pressing system adapted to drive a housing of the additive product container into engagement with a cap member of the additive product container to seal the product chamber of the additive product container; and a gassing system adapted to force a second gas into the product chamber to pressurize the product chamber.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20

Example 23 is a system to implement of any of Examples 1-20.

Example 24 is a method to implement of any of Examples 1-20.

What is claimed is:

1. A sterile filling method for an additive product container defining a product chamber adapted for containing the additive product, the sterile filling method comprising:

forcing a first gas at a first temperature into the product chamber over a first threshold period to heat the product chamber to a first threshold temperature;

dispensing the additive product at a second temperature into the product chamber, wherein the second temperature is between about 84 degrees Celsius and about 95 degrees Celsius;

sealing the product chamber; and rotating the additive product container from a first position to a second position.

2. The sterile filling method of claim 1, wherein forcing the first gas at the first temperature into the product chamber over the first threshold period includes forcing the first gas into the product chamber at a flow rate greater than or equal to 0.5 cubic feet per minute.

3. The sterile filling method of claim 1, wherein the first temperature is between about 153 degrees Celsius and about 157 degrees Celsius.

4. The sterile filling method of claim 3, wherein the first threshold period is between about 45 seconds and about 50 seconds.

5. The sterile filling method of claim 4, wherein the first threshold temperature is between about 139 degrees Celsius and about 141 degrees Celsius.

6. The sterile filling method of claim 5, wherein the sterile filling method further comprises maintaining the additive product container in the second position for a second threshold period after rotating the additive product container from the first position to the second position.

7. The sterile filling method of claim 6, wherein the second threshold period is at least about 20 seconds.

8. The sterile filling method of claim 7, wherein rotating the additive product container from the first position to the second position includes rotating the additive product container between about 120 degrees to about 240 degrees.

9. The sterile filling method of claim 8, wherein sealing the product chamber includes:

inserting a sealing member into the product chamber to establish a fluid tight seal between the sealing member and product chamber.

10. The sterile filling method of claim 9, wherein sealing the product chamber includes pressurizing the product chamber with a second gas.

11. The sterile filling method of claim 10, wherein pressurizing the product chamber with the second gas includes pressurizing the product chamber to a pressure greater than or equal to 110 pounds per square inch.

12. The sterile filling method of claim 11, wherein forcing the first gas at the first temperature into the product chamber includes inserting a first nozzle into the product chamber; and wherein dispensing the additive product at the second temperature includes inserting a second nozzle into the product chamber.

13. The sterile filling method of claim 12, wherein dispensing the additive product at the second temperature into the product chamber includes weighing the product container to verify a volume of the additive product within the product chamber.

14. The sterile filling method of claim 1, wherein rotating the additive product container from the first position to the second position includes rotating the additive product container about a lateral axis of the product container between about 120 degrees to about 240 degrees.

15. A sterile filling method for an additive product container defining a product chamber adapted for containing the additive product, the sterile filling method comprising:

forcing a first gas at a first temperature into the product chamber over a first threshold period to heat the product chamber to a first threshold temperature;

between about 1 second and about 8 seconds after the first threshold period, dispensing the additive product at a second temperature into the product chamber;

between about 10 seconds and about 15 seconds after the first threshold period, sealing the product chamber; and between about 22 seconds and about 52 seconds after the first threshold period, rotating the additive product container from a first position to a second position.

* * * * *